United States Patent [19]

Bracken

[11] Patent Number: 4,935,171
[45] Date of Patent: Jun. 19, 1990

[54] METHOD FOR VESICLE FORMATION

[75] Inventor: Kevin R. Bracken, Sunland, Calif.

[73] Assignee: Vestar, Inc., San Dimas, Calif.

[21] Appl. No.: 303,473

[22] Filed: Jan. 27, 1989

[51] Int. Cl.$^5$ .................... A61K 43/00; A61K 9/127; B01J 13/02
[52] U.S. Cl. ......................... 264/4.6; 264/4.1; 424/450; 436/829; 514/6; 514/832; 514/833
[58] Field of Search .................. 264/4.1, 4.6; 424/450; 159/5, 6.1, 6.2, 6.3

[56] References Cited

U.S. PATENT DOCUMENTS

| | | | |
|---|---|---|---|
| 2,812,019 | 11/1957 | Rasmussen | 159/6.2 X |
| 2,863,888 | 12/1958 | Schurman | 159/6.2 X |
| 2,927,634 | 3/1960 | Gudheim | 159/6.3 X |
| 3,129,132 | 4/1964 | Gudheim | 159/6.3 X |
| 3,261,391 | 7/1966 | Gudheim | 159/6.3 |
| 3,346,034 | 10/1967 | Donovan et al. | 159/6.3 |
| 3,468,849 | 9/1969 | Rothert | 159/6.2 |
| 4,065,346 | 12/1977 | Evkin | 159/6.1 |
| 4,073,677 | 2/1978 | Noda | 159/6.2 |
| 4,093,479 | 6/1978 | Baird | 159/6.2 |
| 4,133,874 | 1/1979 | Miller et al. | 424/450 |
| 4,153,500 | 5/1979 | Feres | 159/6.1 |
| 4,321,106 | 3/1982 | Burkhard et al. | 159/6.2 X |
| 4,485,054 | 11/1984 | Mezel | 264/4.6 |
| 4,526,713 | 7/1985 | Chino et al. | 159/6.2 X |
| 4,710,266 | 12/1987 | Hayashi et al. | 159/7 |
| 4,738,295 | 4/1988 | Genser | 159/6.1 |
| 4,752,425 | 6/1988 | Martin | 264/4.6 |
| 4,753,788 | 6/1988 | Gamble | 264/4.1 X |
| 4,761,288 | 8/1988 | Mezel | 424/450 |
| 4,765,987 | 8/1988 | Bonte | 424/450 |

OTHER PUBLICATIONS

Chemical Engineers' Handbook, Perry et al., pp. 11-27 to 11-36, 1973.
Artisan Industries, A Brief Summary of Artisan Industries' Capabilities, 1987.
Bangham et al., J. Mol. Biol. 13, 238-252 (1965).
Preparation of Liposomes on the Industrial Scale: Problems & Perspectives Chap. 18 in Liposome Technology, vol. I, G. Gregoriadis, Ed. pp. 248-257 (1984).
Brinkman Laboratory Catalog Describing Büchi Rotary Evaporators, pp. 9-12.
Deamer et al., 'Liposome Preparation: Methods and Mechanisms'; in *Liposomes*, M. J. Ostro ed., Marcel Dekker Inc. (1983), p. 36.

Primary Examiner—Richard D. Lovering
Assistant Examiner—John M. Covert
Attorney, Agent, or Firm—Adam Cochran

[57] ABSTRACT

A single-vessel method is provided for preparing liposomes in commercial quantities by forming a homogeneous and uniform lipid film in a thin-film evaporator by evaporation of the organic solvent, followed by in situ hydration of the film in an aqueous phase by agitation with the rotor.

6 Claims, 2 Drawing Sheets

METHOD FOR VESICLE FORMATION

FIELD OF THE INVENTION

This invention relates generally to the formation of lipid micellar particles and more particularly to the commercial production of phospholipid vesicles.

BACKGROUND OF THE INVENTION

Lipid micellar particles in the form of vesicles, also known as liposomes, are known and may be produced in the laboratory through the formation of a lipid film by the rotary evaporation of an organic solvent, followed by the hydration of the lipid film using methods of sonication, dialysis, injection or reverse phase evaporation to form the liposomes.

Such laboratory methods have been difficult to adapt to produce liposomes in commercial quantities. Generally, the lipid film or powder is formed in a first step, for example by spray drying the lipid, and then this film is hydrated in a separate apparatus. For example, an advantageous method for producing significant quantities of small unilamellar vesicles by the hydration of a dried lipid film in a modified homogenizing device is described in U.S. Pat. No. 4,753,788. However, existing methods for the manufacture of liposomes do not provide for the formation and vesiculization of lipid films in a single container, which would provide significant advantages in the production of liposomes, particularly multilamellar vesicles (MLVs), in a sterile environment. Such a method would be advantageous in that MLVs cannot be sterilized by filtration or heat sterilization for pharmaceutical use. In addition, existing art does not provide a method for the effective large scale, single vessel production of liposomes which contain an amphiphilic or lipophilic (i.e., hydrophobic) therapeutic agent which must be dissolved in the lipid film, and the transfer of a drug-containing lipid film from an evaporation vessel to a hydration vessel can involve significant problems.

Accordingly, it has been a desideratum to provide an apparatus and method for both the establishment and hydration of a lipid film to form liposomes in a single vessel in quantities and under conditions which are adaptable to commercial production.

The invention may be briefly summarized as method and apparatus for the vesiculization of an amphiphilic lipid material in an aqueous phase, comprising the use of a modified thin-film evaporator for both the film-forming and lipid hydration steps of liposome formation. More particularly, the invention includes a method for the formation of liposomes, preferably multilamellar vesicles, comprising the steps of introducing a mixture including amphiphilic lipid material (preferably including an amphiphilic or lipophilic biologically active agent) and a liquid into a closed chamber having a cylindrical interior wall, a rotatable shaft disposed coaxially with respect to the wall and having at least one rotor blade secured thereto and extending radially therefrom into a spaced, film-forming relationship with the wall; forming a film of the lipid material on the wall by rotation of the blade and evaporation of the liquid; introducing an aqueous phase into the chamber; and hydrating the film by rotating the blade at a speed which is sufficient to form liposomes.

Preferably, the lipid film is of uniform thickness and essentially all of the liquid which has been introduced into the closed chamber during the film-forming process is evaporated prior to the introduction of the aqueous phase into the chamber.

The method of the invention provides for the use of the described apparatus wherein the film-forming zone between the rotor blade(s) and the wall is of uniform thickness, that is, the zone is free of variations in thickness which produce incomplete or uneven drying of the lipid mixture; and in particular is free of depressions in the wall portion adjacent the rotor blade. The apparatus includes a fluid feed inlet and a fluid outlet in fluid communication with the chamber, each being disposed in a manner which continues the uniform thickness of the film-forming zone, for example neither the inlet or outlet openings are positioned radially adjacent the rotor blades within the zone. Preferably, the fluid outlet is disposed either in an end of the closed chamber outside of the film-forming zone, or comprises a valve which provides a planar surface which is flush with the surface of the closed chamber to maintain such uniform thickness.

Other aspects of the invention will become clear from a reading of the following detailed description of the invention.

DETAILED DESCRIPTION OF THE PREFERRED EMBODIMENT

Thin-film evaporators are well known as continuous feed concentrating apparatus for a variety of solutions, wherein a relatively dilute solution is introduced into the evaporator chamber, a thin film of this solution is formed on an inner, heat exchange surface by blades on a rotor shaft, and the film is moved axially toward a product outlet by fluid pressure on the dilute solution, helical rotor blades or, in the case of vertical evaporators, by gravity. As the thin film is formed heat transmitted through the wall and/or low pressure applied to the chamber evaporates solvent and concentrates the solution, which is continuously extracted, e.g., as a flowable slurry, through a fluid outlet or flows from an open end of the chamber for further processing. Thus, existing thin-film evaporators are continuous flow, i.e., open systems as opposed to the modified thin-film evaporator of the invention in which a closed chamber is employed both for film-forming and film hydration in a batch process.

The invention can be described with respect to the accompanying drawings, in which.

Since the basic structure of thin-film evaporators is well known to those of skill in the art, the description of the apparatus will be general in nature with respect to matters of common knowledge, and will concentrate primarily on novel features which enable use according to the method of the invention.

Figure 1:
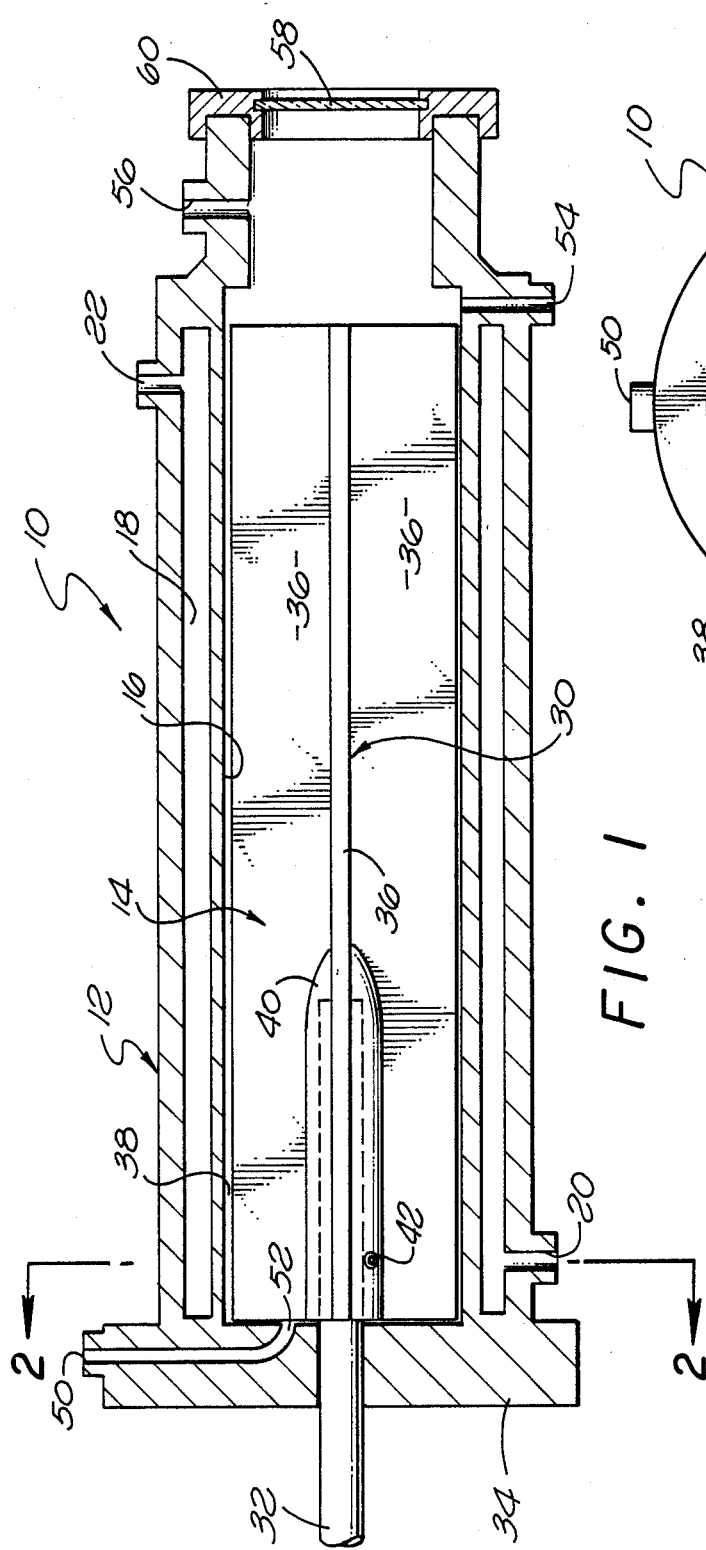
FIG. 1 is a schematic, cross sectional view of a thin-film evaporator apparatus which is adapted to the present invention.
Figure 2:
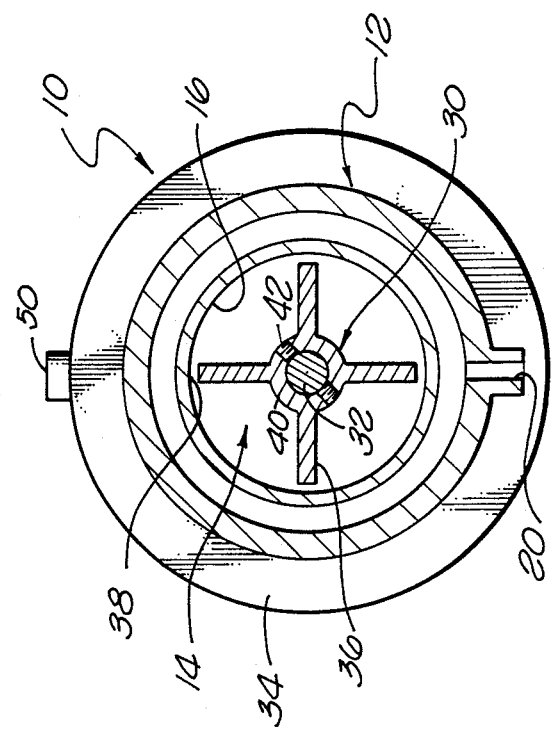
FIG. 2 is a sectional view taken along the line 2—2 in FIG. 1.

FIGS. 1 and 2 are schematic views of a thin-film evaporator, and show an evaporator apparatus 10 comprising a casing 12 which forms a closed or sealable inner cylindrical chamber 14. The chamber 14 is specifically defined by an interior heat transfer wall 16 which transfers heat between the chamber 14 and a thermal exchange jacket 18. Fluid enters the jacket 18 by an inlet 20 and exits the jacket via an outlet 22, cycling from an appropriate external heating or cooling apparatus to provide proper temperature within the chamber 14.

A rotor 30 is positioned within the chamber 14 on a rotatable shaft 32 by a support bearing not specifically shown, within an end flange 34. It will be understood by those of skill in the art that the flange also will include sealing means to enable a significant vacuum, with a pressure as low as 20 microns, to be drawn in the chamber 14. The shaft 32 is driven by an electric motor, not shown, which in this embodiment rotates the shaft at variable speeds of up to 3600 RPM.

Rotor blades 36 are secured to the rotatable shaft for rotation therewith, and extend radially from the rotor shaft axis into a spaced, film-forming relationship 38 with the wall 16 and extend axially along the wall to define a film-forming zone between the rotor blades and a film-forming portion of the wall adjacent the rotor blades, the zone being of uniform thickness and being free of depressions. A wide variety of thin-film evaporator blade and rotor type may be employed in the invention. The term blade, as used herein, is meant to encompass any extension means from a rotating shaft, which is capable of forming a film on the walls of the chamber of a thin-film evaporator.

For most liposome forming solutions, a clearance between the rotor blades and the cylindrical wall should be about 0.75 mm, although the clearance depends primarily on the viscosity of the input solution and can be calculated by one of ordinary skill in the art without undue experimentation. Generally, the greatest efficiency in the process is obtained by maintaining the greatest possible clearance which maintains the homogeneity of the cast film. The rotor 30 is secured to the shaft 32 within a hub member 40, which is disposed at the intersection of the blades 36, by a plurality of threaded fasteners 42 as are shown in FIG. 2.

Feedstock enters the apparatus 10 through an inlet fitting 50 and flows into the chamber 14 via a feed inlet 52. Also shown in FIG. 1 is a stock outlet 54 and a vapor outlet 56 at the opposite end of the casing 12, as well as a sight glass 58 disposed in an end cover 60. The stock outlet valve 54 is positioned at the upper (downstream) end beyond the film-forming zone which is defined by the rotor blades, thus avoiding the depression which would be formed in the wall of the zone if the open outlet were placed radially adjacent the blade (within the zone) as positioned in prior evaporators.

Figure 3:
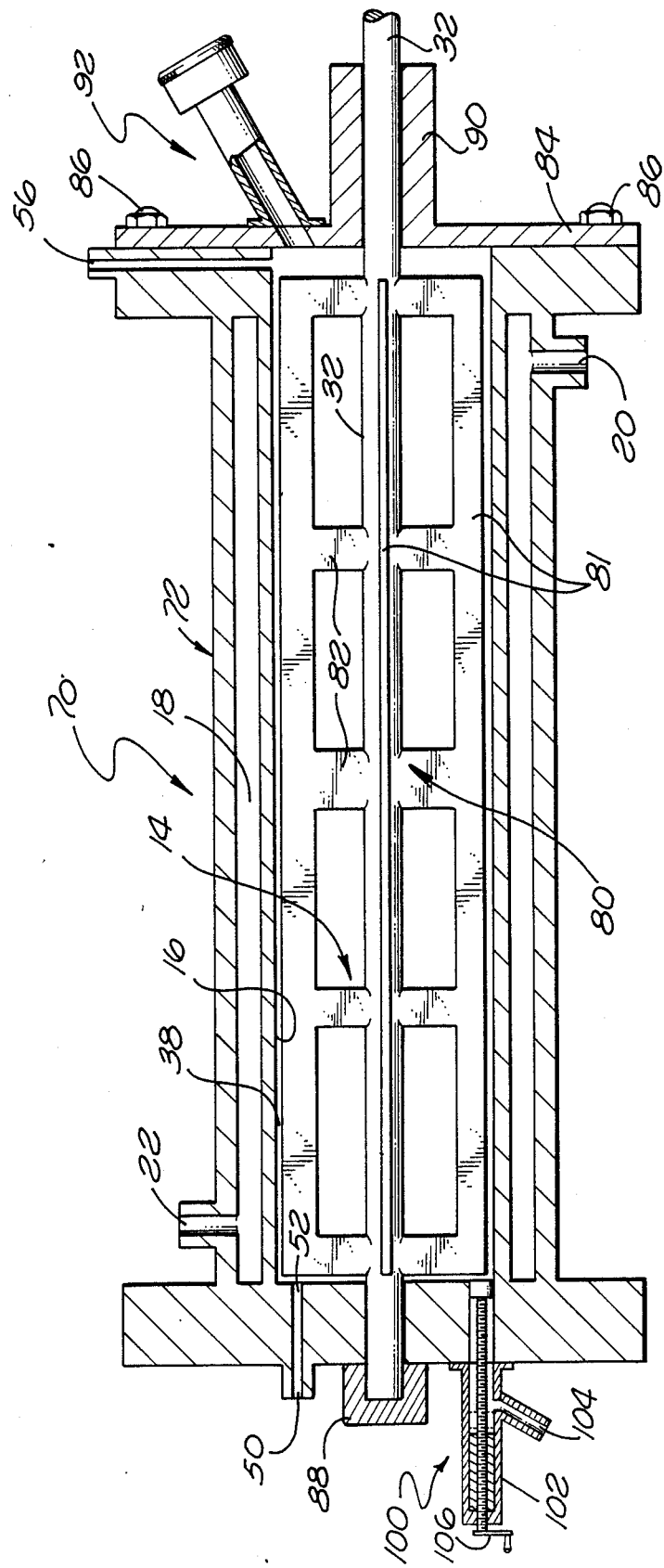
FIG. 3 is a schematic, cross sectional view of an alternative embodiment of an evaporator for use in the invention.

An alternative embodiment is shown in FIG. 3, where identical reference numerals are employed to depict similar features. An evaporator 70 has a casing 72 which includes an inner cylindrical chamber 14. The chamber 14 is again defined in this embodiment by an interior heat transfer wall 16 which transfers heat between the chamber 14 and a thermal exchange jacket 17. Fluid enters the jacket 18 by an inlet 20 and exits the jacket via an outlet 22, cycling as described with respect to FIG. 1.

A rotor 80, in this embodiment including rotor blades 81 spaced from the shaft 32 by supports 82, is positioned within the chamber 14 on a rotatable shaft 32 by support bearings, not specifically shown, within flanges 83 and 84, the latter being attached to the drive end of the evaporator by fasteners 86. It will be understood by those of skill in the art that the flanges also will include sealing means, as indicated schematically by the end portions 88 and 90, to enable a significant vacuum to be drawn in the chamber 14. In practice, the shafts are sealed by water flushed, mechanical-seal stuffing boxes as are known in the art.

The apparatus 70 also includes at least one sight-glass assembly 92, in the flange 84, which permits operator viewing of the contents of the chamber 14. The rotor blades 81 are secured to the rotatable shaft for rotation therewith and, as in the case of the blades 36, extend radially from the rotor shaft axis into a spaced, film-forming relationship 38 with the wall 16 and define a film-forming zone between the rotor blades and a film-forming portion of the wall adjacent the rotor blades, the zone being of uniform thickness and being free of depressions. Feedstock enters the apparatus 10 through an inlet fitting 50 and flows into the chamber 14 via a feed inlet 52, and a vapor outlet 56 is shown at the opposite end of the casing 72.

A stock outlet valve of the type indicated by the reference numeral 100, in the flange 83, has been shown to provide significant advantages. This valve includes a plunger 102 which, when in the closed position as shown in the drawing, occupies the entire inner valve bore leaving a surface which is flush with the inner surface of the chamber 14. The lower portion of the bore of the valve 100 is seen to be even with the lowest edge of the cylindrical wall 16 so that complete drainage of the hydrated solution from the chamber is ensured.

The valve 100 includes a body 103, and inlet tube 104 and a handle-threaded stem assembly designated by the reference numeral 106 which operates to retract and advance the plunger 102. Valves of this type are manufactured and sold by the Fetterolf Corporation of Skippack, Pa. under the trademark RAM-SEAL.

In the operation of the apparatus, it will be understood that the film-forming lipid must be maintained within the zone 38 during the influx and evaporation of the liquid. Preferably, for this reason, it is important to maintain the thin-film evaporator at an angle of from 5°–10° from horizontal with the inlet end (the flanges 34 and 83 in FIGS. 1 and 3, respectively) at the inferior position.

The process begins with the preparation of a solution or dispersion of materials capable of being hydrated to form liposomes, such materials being known to those of skill in the art. A variety of amphiphilic lipid materials may thus be employed with the method and apparatus of the invention. Preferably, phosphoglycerides or phospholipids such as dipalmitoyl and distearoyl phosphatidylcholine alone or in combination with cholesterol are dissolved in chloroform, ethanol or other organic solvents. As described in the examples, one or more consecutive films may be formed in the evaporator prior to hydration.

If a lipophilic or amphiphilic agent or drug is to be included in the liposomes, this agent can be included in the lipid solution. Hydrophilic agents may be included in the hydrating solution. Any therapeutic or diagnostic agent which may be incorporated into liposomes according to laboratory procedures may be employed to form the MLVs according to the invention, although superior results have been shown in the encapsulation of anthracyclines such as doxorubicin. If SUVs are desired, the suspension extracted from the thin-film evaporator may be further processed, for example, in the modified homogenizing device as described in U.S. Pat. No. 4,753,788 to form smaller vesicles.

Methods and materials for the preparation of such solutions of amphiphilic materials are known in the art and will not be described in detail herein. If the liposomes are to be used for pharmaceutical purposes, the preparation is made under aseptic conditions. This is done by sterilizing the evaporator chamber, by autoclaving or steam-in-place techniques depending on the particular size of the evaporator, and feeding and extracting the stock under sterile conditions, e.g., all inlet fluids being fed into the chamber through sterile filters.

The lipid solution is introduced into the apparatus, while the rotor is operating, via a conduit attached to the inlet fitting 50 and drawn by a low pressure, for example, about 68 cm of mercury, which is produced by a vacuum pump attached to the vapor outlet 56. Alternatively, a peristaltic pump can be employed to load the chamber. While the rotor has been operated at a speed of 3600 RPM in the following examples, significant variation in the rotor speed is possible and the optimal speed for a particular lipid can be determined visually through the sight glass, by adjustment of the variable speed motor drive of the evaporator, without undue experimentation.

The amount of solution required to fill the chamber may be determined experimentally by use of the sight glass at the upper end of the apparatus. As the solution is drawn into the chamber, the centrifugal force distributes the liquid on the interior heat-transfer walls, the temperature of which is maintained at about 30° C. (for the solvent chloroform) by recirculating water of appropriate temperature in the thermal exchange jacket. Simultaneously, a low vacuum is drawn on the chamber, typically 50–72 cm Hg. The solvent in the solution on the walls of the chamber thus evaporates and is drawn from the chamber through the outlet 56. Since the inlet 52 is disposed at an upper edge of the chamber, the inlet may be pumped dry of lipid and solvent as the chamber is filled to avoid residual unevaporated solvent in the chamber during hydration.

The amount of solution introduced into the chamber is initially determined by viewing through the sight glass and maintaining liquid flow until the liquid reaches the end (top) of the film-forming zone, i.e., the downstream end of the rotor. At this point, the influx of solution is halted, allowed to dry, and then additional solution is added until the rotor initiates vibration which indicates that the rotor tips are dragging on the film in the chamber, and thus that maximum capacity has been reached. The total amount of solution added can be measured in a first run, and this amount can be employed in subsequent procedures.

After the casting of the film, the rotor is halted and the film may be subjected to an increased vacuum (ca. 100 microns pressure), if necessary, for at least about ½ hour to dry the film completely. This is followed by purging the chamber slightly with air or preferably an inert gas such as nitrogen (admitted through the inlet 50) to relieve the high vacuum. The hydrating solution is then admitted through the inlet 50, the amount thereof being determined by the desired concentration of the liposome dispersion.

During this filling and hydrating step, the material may be constantly purged with nitrogen to avoid oxidation of the components. The operation of the rotor is then resumed for a time sufficient for liposome formation, preferably from one-half to one hour, during which the agitation of the rotor pulls the film from the wall and forms vesicles in the aqueous phase. The temperature of the interior wall in the following examples is maintained at about 30° C. during the hydration procedure, although other temperatures could be advantageously employed with alternative mixtures. Following liposome formation, the aqueous dispersion is removed from the chamber via the stock outlet while maintaining the nitrogen purge.

Following the removal of the dispersion, the apparatus can be easily cleaned by use of appropriate solvents. For example, the lipids may be removed with a sodium hydroxide solution, and solvents for the therapeutic agents, e.g., bleach for doxorubicin HCl, will be readily apparent.

EXAMPLE I

Formation of 2:1 DSPC/CHOL Multilamellar Vesicles

This example describes the use of an Artisan ¼ sq. ft. thin-film evaporator, shown schematically in FIG. 1, for the production of films and hydration of films to liposomes In this evaporator, the housing volume was 385.98 cm$^3$ (including the space occupied by the rotor) and the maximum capacity of the space between rotor and housing was calculated for charging volume.

| | |
|---|---|
| Housing inner diameter: | 50.80 mm ± 0.05 |
| Rotor outer diameter: | 49.28 mm ± 0.05 |
| Clearance = 1.524 mm | Rotor Length = 190.5 mm |
| Zone volume = 190.5 pi [(50.8/2)$^2$ − (49.28/2)$^2$] | |
| = 22754 mm$^3$ × 0.001 | |
| = 22.75 cm$^3$, about 23 ml | |

Distearoylphosphatidylcholine (DSPC) and cholesterol (CHOL) were mixed in a two to one molar ratio (DSPC:CHOL 2:1) at a concentration of 36% w/v in CHCl$_3$. The rotor was energized at 3600 RPM and the vacuum in the chamber was set to about 250 mm Hg by opening a valve on a vacuum pump connected via tubing to the vapor outlet 56.

A needle valve in the inlet tubing was opened, and about 24 ml of the DSPC:CHOL solution was drawn into the chamber by the vacuum, until visible through the sight glass at the end of the housing. The vacuum in the chamber was increased to 69 cm Hg with continued rotation, and it could be observed that a thin film was drying as seen by a flashlight beam through the sight glass. The operations described in this paragraph took about 2 minutes.

When it appeared that a film had fully formed in the zone, the rotor was turned off, the vacuum line to the chamber was closed and the vacuum pump was disconnected. A larger, Kinney vacuum pump was connected and energized to a vacuum of >740 mm Hg. The film "popped" during this high vacuum drying and appeared to come off the housing interior in sheets. This higher vacuum drying process lasted about ½ hour. This vacuum was released using filtered dry air.

The chamber was then heated to about 65° C. by circulation of hot water in the thermal exchange jacket, and the chamber evacuated to about 685 mm Hg with a small vacuum pump. The vacuum line was then closed. 200 ml of 0.9% saline (also at a temperature of 65° C.) was then drawn through the inlet by the vacuum in the chamber. At this point, the rotor was again energized at 3600 RPM.

After 10 minutes of agitation the agitated suspension was extracted, by a peristaltic pump on a pickup tube attached to the stock outlet, into a collection flask. The rotor was off during this extraction operation, and the needle valve in the inlet tubing was opened to permit air to equalize pressure during the extraction. An additional 100 ml of 0.9% saline was added by a similar procedure and pumped into the same collection flask.

The collected suspension was analyzed for liposome size with a Coulter counter. A normal Gaussian distribution of MLVs was shown:
Mean by number difference 4.7 microns
10% greater than 7.75 microns
50% at 5.04 microns
90% less than 3.23 microns.

EXAMPLE II

Preparation of MLV Encapsulated Doxorubicin 150 mg doxorubicin (along with 750 mg lactose excipient) and 225 mg cardiolipin in ethanol (total 50 ml) were dissolved in 150 ml methanol and mixed together briefly in a flask under sterile conditions. Sterile tubing was placed in the flask and connected to the stock inlet of a sterilized Artisan ¼ sq. ft. thin-film evaporator shown schematically in FIG. 1. The rotor was energized at 3600 RPM and the vacuum in the chamber was set to 25.4 cm Hg by opening a valve on a vacuum pump, thus drawing doxorubicin/lipid solution into the chamber until the film-forming zone was filled as seen through the sight glass. All vacuum and extraction tubing and apparatus in this procedure was sterilized.

The temperature in the water jacket and end seal, and in a condenser attached to the vapor outlet 56, was monitored over time, as was the chamber vacuum. The results being as follows:

| Time(min) | Jacket °C. | Seal °C. | Vacuum mm Hg | Condenser °C. |
|---|---|---|---|---|
| 1:45 | 28.4 | 19.2 | 673 | 4.7 |
| 6:45 | 28.4 | 19.4 | 673 | 4.9 |
| 11.22 | 28.3 | 19.6 | 673 | 5.2 |
| 14:00 | 28.5 | 19.7 | 673 | 5.4 |
| 15:40 | — | 19.6 | 679 | 5.5 |

At 15:40 the rotor was turned off, and a vacuum of greater than 740 mm Hg was applied to the chamber for about 30 minutes to further dry the film, although a shorter drying time after the formation of this first film is preferred to reduce dust carryover.

A second sterile lipid solution was made consisting of 562.5 mg egg phosphatidylcholine (PC), 188.1 mg cholesterol and 56.2 mg stearyl amine in 100 ml chloroform. After drawing nitrogen into the chamber to relieve the high vacuum, the previous lower vacuum was applied to the chamber to draw the second lipid solution therein. Again, the temperature in the water jacket, end seal and condenser, and the chamber vacuum, was monitored during the procedure. The results being as follows:

| Time(min) | Jacket °C. | Seal °C. | Vacuum mm Hg | Condenser °C. |
|---|---|---|---|---|
| 3:10 | 27.5 | — | 546 | 4.4 |
| 7:30 | 27.2 | 20.3 | 584 | 4.6 |
| 10:08 | 27.1 | — | 584 | 4.7 |
| 14:00 | 27.8 | — | 673 | 4.8 |

The feed was disconnected at about 10 minutes, and rotor vibration at 12:55 minutes indicated that maximum capacity had been reached. Condensation drips stopped in the condenser at 14:30, indicating a dry film. At 16:10 minutes, the rotor action was discontinued, and the higher vacuum was applied.

Next, 75 ml of 20 mM sodium pyrophosphate buffer in 9% lactose with 0.47 ml 1M NaOH (buffer solution pH 9.19) was added via vacuum, and the rotor was turned on at 3600 RPM. The temperature in the water jacket during this hydration step was 27.5° C., and rotation was continued for 15 minutes. The pH after hydration was 9.06, and the volume collected from the outlet 54 was 62 ml. This collectant was divided into 32 ml and 30 ml aliquots in separate vials. The liposome suspension in one vial was neutralized with 18 ml 1M HCl to pH 7.48 and the liposomes in both vials were analyzed for doxorubicin concentration, which was shown to have been entrapped in the sterile MLVs which were formed.

Pharmaceutical evaluation of MLVs formed by this procedure were equivalent, both in pharmacokinetics and biodistribution characteristics, when compared to this formulation of liposomes made by the traditional laboratory methods of rotary evaporation and bath sonication.

EXAMPLE III

This example describes the use of the Artisan ¼ sq. ft. thin-film evaporator for the production of liposomes encapsulating hemoglobin. 5.92 g hydrogenated soy phosphatidylcholine (HSPC), 2.62 g cholesterol, 0.51 g dimyristoylphosphatidylglycerol (DMPG) and 0.15 g alpha-tocopherol (an anti-oxidant) were dissolved in 60 ml $CHCl_3$ with heat and stirring.

The rotor was energized at 3600 RPM and the solution was drawn into the chamber of the thin-film evaporator by vacuum, until visible through the sight glass at the end of the housing. The temperature in the water jacket was maintained at 28° C. After film formation as described above, the rotor was stopped and the pressure was reduced within the chamber for complete drying of the film which was observed through the use of a flashlight shown through the sight glass. The film-forming and drying process lasted about three hours.

The chamber was then heated to about 32° C. by circulation of hot water in the thermal exchange jacket, and a dispersion of 28 wt % hemoglobin in phosphate buffered saline was drawn into the chamber with the small vacuum pump. A total of 317 g of 28 wt % hemoglobin was added to the chamber. The rotor was again energized at 3600 RPM.

After one hour of agitation the agitated suspension was extracted into a collection flask. The rotor was off during this extraction operation.

The collected suspension was analyzed for particle size with a Coulter counter, showing a mean diameter of 3.1 micron, typical of MLVs. A hemocrit assay developed by the Naval Research Laboratory to measure the percent of liposome encapsulated hemoglobin demonstrated a range of two to eight percent hemocrit, indicating hemoglobin encapsulated in the liposomes.

From the foregoing description the essential characteristics of the invention can be readily ascertained and, without departing from the spirit and scope thereof, the invention can be adapted to various usages. Changes in form and substitution of equivalents are contemplated as circumstances may suggest or render expedient, and although specific terms have been employed herein, they are intended in a descriptive sense and not for purposes of limitation.

I claim:

1. A batch method for the formation of liposomes, comprising the steps (a) introducing a mixture comprising amphiphilic lipid material and an organic solvent in which the lipid is soluble into a chamber having a cylindrical interior heat transfer wall which transfers heat between the chamber and a thermal exchange jacket, a rotatable shaft disposed coaxially with respect to the wall, and at least one rotor blade secured to the rotatable shaft for rotation therewith and extending radially therefrom into a spaced, film-forming relationship with the wall;

(b) forming a film of the lipid material on the wall by rotation of the blade and evaporation of the liquid;

(c) introducing an aqueous phase into the chamber; and (d) hydrating the film by rotating the blade at a speed which is sufficient to form liposomes.

2. The method of claim 1 in which the amphiphilic lipid material includes a phospholipid.

3. The method of claim 1 or 2 which further includes the step of drying the lipid film prior to introducing the aqueous phase into the chamber.

4. The method of claim 3 in which the chamber further includes a fluid feed inlet and a fluid outlet, each in fluid communication with the chamber and being disposed outside of the film-forming zone.

5. The method of claim 3 in which the chamber further includes a fluid feed inlet and a fluid outlet, the fluid outlet being disposed in a planar end of the closed chamber outside of the film-forming zone.

6. The method of claim 3 wherein the fluid outlet comprises a valve which provides a planar surface which is flush with the planar end of the closed chamber.

* * * * *